United States Patent
German et al.

(10) Patent No.: US 6,724,958 B1
(45) Date of Patent: Apr. 20, 2004

(54) HANDHELD LASER SYSTEM EMITTING VISIBLE NON-VISIBLE RADIATION

(75) Inventors: John D. German, Cedar Crest, NM (US); Steven J. Saggese, Albuquerque, NM (US); Michael D. Tocci, Sandia Park, NM (US)

(73) Assignee: Science & Engineering Associates, Inc., Albuquerque, NM (US)

( * ) Notice: Subject to any disclaimer, the term of this patent is extended or adjusted under 35 U.S.C. 154(b) by 0 days.

(21) Appl. No.: 09/235,487

(22) Filed: Jan. 22, 1999

Related U.S. Application Data

(60) Provisional application No. 60/072,277, filed on Jan. 23, 1998.

(51) Int. Cl.⁷ .................................................. G02B 6/32
(52) U.S. Cl. ......................................................... 385/33
(58) Field of Search ...................... 385/15–35, 115–125, 385/52; 606/1–17, 170, 180, 139, 194, 39, 108; 356/457, 41

(56) References Cited

U.S. PATENT DOCUMENTS

| | | | |
|---|---|---|---|
| 4,458,683 A | * | 7/1984 | Saito et al. .................... 606/3 |
| 5,074,861 A | | 12/1991 | Schneider et al. |
| 5,147,349 A | * | 9/1992 | Johnson et al. ................ 606/15 |
| 5,209,776 A | | 5/1993 | Bass et al. |
| 5,272,716 A | | 12/1993 | Soltz et al. |
| 5,292,362 A | | 3/1994 | Bass et al. |
| 5,553,629 A | * | 9/1996 | Keipert et al. ............... 128/898 |
| 6,252,511 B1 | * | 6/2001 | Mondshine et al. ......... 340/636 |

OTHER PUBLICATIONS

Kirsch, Andrew J. *Laser tissue soldering: State of the Art*, Contemporary Urology, Oct. 1997, pp. 41–60.

* cited by examiner

*Primary Examiner*—Tu T. Nguyen
(74) *Attorney, Agent, or Firm*—Perkins Smith & Cohen LLP; Jacob N. Erlich; Orlando Lopez

(57) ABSTRACT

A laser system for use in medical, industrial, commercial or research applications in which the location and energy and power density of a nonvisible (e.g., infrared or ultraviolet) laser beam is defined by a plurality of visible beams. Collimating optics are used to direct both the nonvisible and visible beams on the target, such that when the visible beam is in focus on the target, the nonvisible beam has the optimum energy and power density. One implementation of the invention is a self-contained hand-held surgical laser that provides surgeons with the optimal laser beam parameters for laser tissue soldering.

43 Claims, 12 Drawing Sheets

HANDHELD LASER SYSTEM EMITTING VISIBLE NON-VISIBLE RADIATION

This application claims priority from Provisional Patent Application Ser. No. 60/072,277, filed Jan. 23, 1998.

The U.S. Government has certain rights in this invention, in accordance with the terms of SBIR Contract No. F29601-98-C-0006 awarded by the U.S. Air Force.

FIELD OF THE INVENTION

This invention relates to manually-directed lasers that emit beams that are not readily visible to the naked eye, such as lasers used for medical applications (e.g., laser tissue soldering), and lasers used in industrial, commercial or research applications.

BACKGROUND OF THE INVENTION

Manually-directed lasers are used in medical and in industrial applications to direct energy at a target. When the lasers operate at wavelengths which are not readily visible, e.g., near-infrared, infrared, or ultraviolet wavelengths, or when a laser beam which emits visible radiation is pulsed so that it might not be emitting when the operator is aiming the laser beam, it is difficult for an operator to direct the beam at the proper location on the target. One method for resolving this problem is to use a visible beam that is collinear with the non-visible beam. However, that method is often not satisfactory because it does not identify the complete area that is covered by the laser beam, and because it requires a mixing of the optical sources, such that the visible beam and the nonvisible beam are traveling along the same optical path. Furthermore, that method provides no guidance as to whether the correct energy density has been delivered to the target.

A primary medical application that requires delivering energy via laser beams is laser tissue soldering (LTS), as described by Kirsch in Contemporary Urology (Oct. 97, pp. 41–60), which is incorporated by reference herein. LTS is a wound healing technique which bonds the edges of the wound using a protein-based solder activated by energy from a laser. The solder is typically (but not necessarily) mixed with a photon-absorbing dye (or chromophore). The laser used emits electromagnetic radiation at a wavelength absorbed by the photon-absorbing dye and/or the protein-based solder. Solders based on human albumin provide the best strength and leak point pressure upon repair, but various other proteins, including egg albumin, fibrinogen and fibrin have been used. Hyaluronate has been added to solders to increase its viscosity, and may also help cell migration during healing.

Laser tissue welding is a technique which is similar to laser tissue soldering, excpet that it does not use a solder. In that application, the heat is applied directly to tissue with a laser beam.

Many laser-chromophore combinations have been tried. Most studies used the combination of indocyanine green dye (ICG) and a 810 nm diode laser. Laser tissue surgery has been tested successfully in many types of surgery, and is particularly suited for procedures performed on the urinary tract. The advantages of LTS include minimal tissue handling, maximal tissue alignment, maintenance of luminal continuity, water-tight closure, early re-ephithelialization, maximal tensile strength during early healing, no foreign body reaction, and minimal scar formation.

Initially, the typical laser used for LTS (as well as for the related technique, laser tissue welding, which does not use solder) was a relatively large, high-power laser, such as a Nd:YAG laser or a $CO_2$ laser mounted on a bench top. The laser beam was transmitted through a fiber optic cable or through an articulated arm to a hand-held tool. The hand-held tool would be used by the surgeon to direct the laser beam at the tissue to be treated. However, infrared and near-infrared lasers such as the $CO_2$ and Nd:YAG lasers (as well as the 810 nm diode laser mentioned above) are not visible to the naked eye.

More compact laser devices for surgery have been recently developed, e.g., as disclosed in U.S. Pat. No. 5,074,861 issued to Schneider et al. ("Schneider"), U.S. Pat. No. 5,272,716 issued to Soltz et al. ("Stoltz"), and U.S. Pat. No. 5,553,629 issued to Keipert et al. ("Keipert"), which are all incorporated by reference herein. Schneider discloses an erbium YAG laser that transmits the laser energy from the laser to the tip of the probe using a light horn or mirrors. Soltz discloses a semiconductor laser diode system which utilizes two lasers: one laser is a guide laser, providing visible radiation, and one laser supplies the energy to the "workpiece." The two lasers are focused and collimated by a pair of lenses so that they travel identical paths. Keipert et al. disclose a laser apparatus which includes infra-red viewing goggles, so that the surgeon (or other operator of the device) could see the infrared beam.

U.S. Pat. No. 5,147,349 issued to Johnson et al. discloses an infrared diode laser for use in transcutaneous laser photocoagulation of the retina. This laser is optimized for use in the retinal surgery. The specification also discloses the use of a visible laser beam, such as a He-Ne laser, which is optically merged with the infrared diode laser beam, so that the merged beam is visible. However, this system does not define the incident area of the nonvisible beam, or provide any method for determining whether the correct power density and energy density is being delivered to the target.

OBJECTS OF THE INVENTION

Accordingly, it is an object of the present invention to provide the correct energy density (for pulsed systems) and power density (for continuous systems) to a well defined target area when using a laser system with a nonvisible laser beam.

It is a further object of the present invention to provide a hand-held self-contained laser system which has been optimized for use in medical procedures such as laser tissue soldering or laser tissue welding, as well as in industrial, commercial or research applications.

It is also an object of the present invention to provide a method of use of a laser system with a nonvisible beam for laser tissue soldering and for laser tissue welding.

Definitions

"Manually directed" as used herein with reference to directing a laser beam means that the laser beam is directed by a human operator, whether that operator holds a hand-held laser in his hand, holds an aiming tool connected to a laser by an optical fiber, or uses mechanical, electric, electronic, automated or computerized controls to physically direct the laser beam.

A "nonvisible beam" is a beam that is not visible to the operator of the laser system at the time the operator needs to direct the laser for a variety of reasons, including (1) the beam is a near-infrared, infrared or ultraviolet beam that is not readily visible to the naked eye; (2) the beam is pulsed; (3) the laser must be precisely directed before it is turned on;

(4) the operator is wearing safety goggles which block the wavelength of the laser beam.

The "optimum distance" is the distance from the output of the collimating lens at which the power density of the nonvisible beam is at a broad maximum.

SUMMARY OF THE INVENTION

The present invention is a laser system that provides a collimated nonvisible laser beam output, and one or more (laser or non-laser) visible beams that define the location and periphery of the nonvisible beam, and that provide feedback to a human operator such that the operator can maintain the optimum energy/power density at the target. The system comprises at least one nonvisible laser source optically coupled to an optical fiber, at least one visible (laser or non-laser) source optically coupled to one or more optical fibers that deliver visible beams that define the location and periphery of the nonvisible beam at the target, and collimating optics for collimating both the nonvisible laser beam and the visible beams. The collimating optics focus the visible beam such that, when the visible beam is in focus at the target, the nonvisible beam has the optimum energy/power density at the target.

FIG. 1a illustrates the divergence of a beam from an uncollimated fiber 1. FIG. 1b shows the beam profile when collimating optics 2 are placed in front of fiber 1. At about position 4, which is at a distance bb from the output of the collimator, the spot size of the beam is relatively constant over a certain range, i.e., the power density of the beam will not vary greatly over that range on either side of position 4. This characteristic is illustrated by the collimated beam example shown in the line plot with the solid circles in FIG. 2a, where position 4 in FIG. 1 corresponds to the center of the broad maximum at a distance of 14 cm on the abscissa of FIG. 2a. Over a range of 4 cm on either side of 14 cm, i.e. from 10 cm to 18 cm, the power density of the beam is 15±2 watts/cm$^2$, a variation of about ±14% over the 8 cm. The line plot without solid circles in FIG. 2a is a representation of the power variation as a function of distance for an uncollimated beam (the units on the y-axis apply only to the collimated beam plot, and do not apply to this line plot). As FIG. 2a shows, the uncollimated beam is reduced by roughly a factor of three over 8 cm. FIG. 2b is another example of a collimated beam output. This Figure shows that the power density is roughly constant, for this example, over a 5 cm range. FIG. 2c is an example of the laser power density for an uncollimated beam. This plot shows a very steep decline in the power density, and a relatively short working range for the device. For example, if the power density needs to be at 5 watts/cm, FIG. 2c shows that laser system should be positioned at a distance of 1.1 cm from the target area. A change of only 1 mm on either side results in a change of roughly 20% in power density.

Preferably, the power (or energy, for pulsed systems) density should vary by no more than 10% per cm over a range of 2 cm on either side of the optimum distance. Also, the visible light beam should be in sharp focus at approximately the optimum distance, i.e., within 5 mm from the optimum distance.

FIG. 3 is a schematic diagram of the basic components of the present invention. As shown in FIG. 3, the beams from nonvisible laser 9 and visible light source 10 are optically connected using optical fibers 5 and 6, respectively. Visible light source 10 is, e.g., a light emitting diode emitting green light. Visible light source 10 could also emit orange or yellow light, or any other color or mix of colors (including white light) which provides good contrast on the target, and which is readily seen through the protective goggles the operator may be wearing. Optical fiber connector 7 is used to position the optical fiber(s) from the nonvisible laser(s) at the center of the bundle of optical fibers, i.e., the optical fiber carrying the nonvisible beam is surrounded by two or more optical fibers carrying the visible light beams. Collimating lens 8 collimates the light output from optical fibers 5 and 6.

For most applications the present invention uses one nonvisible laser 9 and one optical fiber 5 for the nonvisible Laser beam. Optical fiber 5 is surrounded by two, three, four or more optical fibers from the visible light source (s), as shown in FIGS. 4a, 4b, 4c, 4d, 4e, 4f, and 4h although use of multiple nonvisible optical fibers is also possible, as shown in FIG. 4g. The present invention is preferably implemented with at least six optical fibers (FIG. 4d) and more preferably with at least eight optical fibers (FIG. 4e). Collimating optics 8 are used to collimate the nonvisible beam and the visible light beams, such that both the visible beams and the nonvisible beam are in focus on the target when the laser output is positioned at the optimal distance from the target. This effect is illustrated in FIG. 4i, which shows the appearance of the spots on the target from the visible light beams in sharp focus when the laser output is at the optimal distance from the target (the middle drawing) compared to when the laser output is too close (the left drawing) or too far away (the right drawing)Dark lines 17 on FIG. 4i outline the size of the nonvisible beam at the target as a function of the distance of the laser output from the target. At the optimal distance the size 15 (preferably 1.5 mm to 10 mm in diameter) of the nonvisible beam is at a very broad and shallow minimum (corresponding to a broad maximum in energy density), as shown in the middle drawing of FIG. 4i.

FIGS. 4j and 4k illustrate a second preferred embodiment of the present invention. As shown in FIG. 4j, the optical fiber used to transmit the nonvisible laser beam for the embodiments of the invention shown in FIGS. 4a–4i consists of a central core 20 and an outer cladding 21. In the second preferred embodiment, shown in FIG. 4k, the optical fiber consists of an inner cladding 22 in addition to the central core 20 and the outer cladding 21. In this embodiment, the nonvisible laser beam is transmitted through central core 20 and the visible light beam is transmitted through inner cladding 22. The output of the fiber shown in FIG. 4k is thus a nonvisible laser beam within a ring of visible light.

An example of a specific hand-held implementation of a preferred embodiment of the present invention is described below as Example 1. This implementation is particularly well-suited for laser tissue soldering. In Example 1, the laser is incorporated in a battery-powered self-contained hand-held apparatus with a roughly uniform distribution of light intensity across the beam. The laser apparatus provides laser energy at a wavelength absorbed by the chromophore utilized in the laser solder with optimum parameters for tissue soldering.

DETAILED DESCRIPTION OF EMBODIMENTS OF THE INVENTION

The present invention will be further described through the use of three examples. The first example is a detailed description of a hand-held implementation of the preferred embodiment of the invention. The second example describes the use of the apparatus of the first example for laser tissue soldering. The third example illustrates an advantage of the present invention over the prior art.

The following examples are provided as representative implementations and uses of the present invention, but are not meant to limit or restrict the scope of the invention claimed herein. For example, the apparatus described in Example 1 is a hand-held self-contained laser, whereas the present invention may be practiced with a wide variety of different laser systems, as discussed above. Also, the method described in Example 2 uses a solder and a dye, but the present invention can be practiced, in some applications, without the use of either a solder or a dye (in which case the procedure would be called laser tissue welding) or with a solder but not a dye.

EXAMPLE 1

Figure 5:
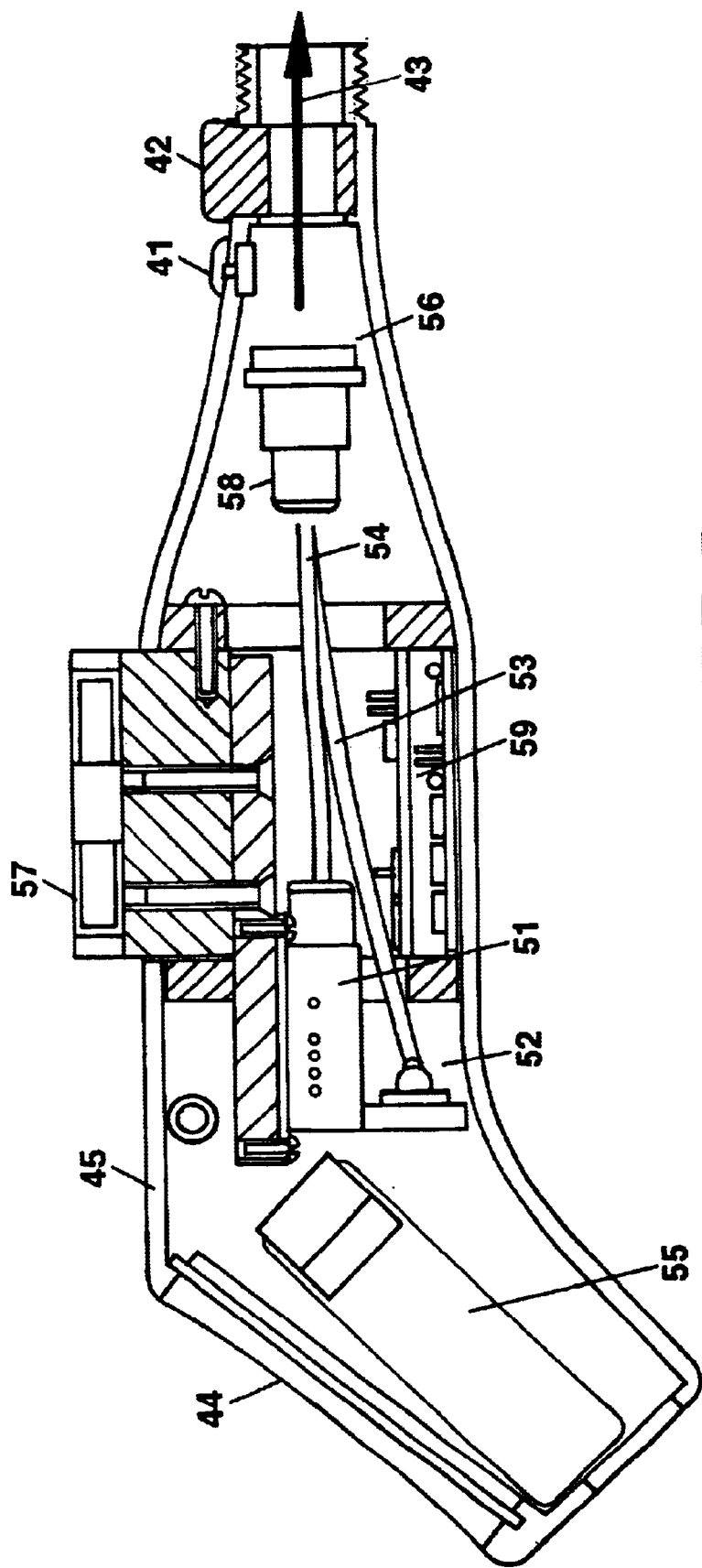
FIG. 5 is a side cross-sectional view of the implementation of the present invention described in Example 1.

The primary components of the hand-held implementation of the present invention described in this Example are shown schematically in FIG. 5. The apparatus consists of laser diode 51, visible light sources 52, a fan-cooled finned heat sink 57, optical fibers 53 transmitting the visible light beam (nine optical fibers were actually used), optical fiber 54 transmitting the nonvisible laser beam, optical fiber connector 58 which holds optical fibers 53 and 54 in optical contact with fiber collimating lens 56, a power supply such as NiCd or Li-ion batteries 55, laser activation switch 41, manual shutter 42, display/control panel 44 and laser housing 45. Optical fiber connector 58 centers optical fiber 54 in the middle of optical fibers 53, such that the visible beams emitted from the ends of optical fibers 53 define the position of nonvisible beam 43 emitted from the end of optical fiber 54 and transmitted by collimating lens 56.

Laser diode 51 is a High Power Devices Model No. HPD1020-BUTF-79020 (New Brunswick, N.J.) which is a nominal 2-watt device. After coupling losses in the optical train, a maximum of 1.5 watts of laser power can be delivered to the target. In general, the wavelength is selected to provide a good match to the absorption peak of the dye in the solder. In this Example, the wavelength of infrared electromagnetic radiation produced by the High Power laser is approximately 800±30 nanometers. Although this wavelength was originally developed to provide pump energy to solid state lasers, it also falls in a primary absorption band for indocyanine green dye (the laser-absorbing dye used in formulating the tissue solder, an important anticipated use of the present invention). Although a portion of the laser radiation is perceived as red light by the operator with the naked eye (due to the high power of the laser), the operator generally wears protective goggles (to prevent eye injury from the nonvisible laser beam), and these goggles prevent this perception. Moreover, the infrared radiation is only present when the laser is actually being used, and so the operator cannot aim the laser beforehand.

The heat generated by laser diode 51 is dissipated using heat sink 57. The power supply of this implementation of a preferred embodiment of the present invention utilizes Sony Li-ion battery Model No. NP-F550, 7.2 V, 10.8 Wh. This battery provides enough energy for up to 45 minutes of surgery, depending on how often the laser is switched off during use.

Figure 6:
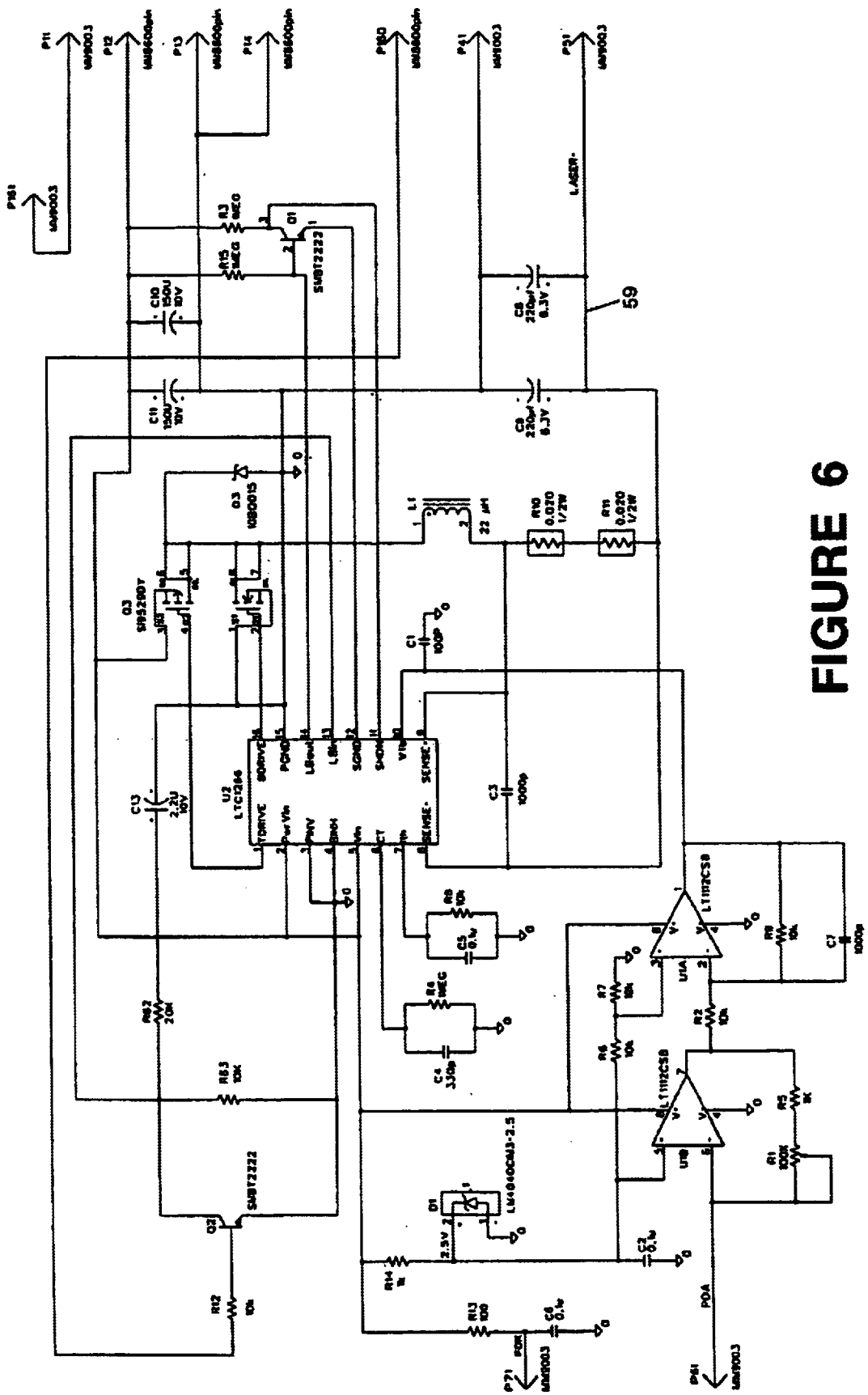
FIG. 6 is an electronic diagram of the high efficiency laser power supply of the system of Example 1.

There are two switches on the preferred embodiment of Example 1. First, a master switch on control/display panel 44 turns the power on to the electronic power supply circuit and the heat sink cooling fan. Once this switch is on, the surgeon can press or release push-button switch 41 to turn on or turn off the laser beam. Power to the laser diode is generally controlled by power supply circuit 59, schematically diagrammed in FIG. 6. This circuit supplies current-controlled power, with a photodiode feedback loop, to the laser diode to maintain the intensity of the infrared radiation produced by the laser diode at the level specified by the operator. The top four connections on the right of FIG. 6 (P11, P12, P13 and P14) are connections to the battery. The next three connections, P160, P41 and P51 are connected to the laser enable, laser cathode and laser anode connections, respectively. On the left of FIG. 6, P71 and P61 are connected to the photodiode cathode and photodiode anode connections, respectively.

In addition to the master switch, control/display panel 44 preferably includes a pulse counter (to count the laser pulses), a laser "on" light to show when the laser is turned on, a "standby" light, and error LEDs indicating, for example, that the temperature of the laser diode is unacceptably high, or that the battery is low.

As shown in FIG. 5, the nonvisible beam from laser diode 51 is transmitted through optical fiber 54 to optical fibber connector 58. Likewise, the visible light beams are transmitted through optical fibers 53 to optical fiber connector 58. Optical fiber connector 58 is essentially a hollow cylinder into which optical fibers 53 and 54 are positioned and held in place using an adhesive (e.g., an epoxy). The ends of optical fibers 53 and 54 are polished, hard positioned prior to collimating lens 56. Optical fiber connector 58 threads into the assembly for collimatinc lens 56. As an example, an 8-mm focal length, 0.50 numerical aperture lens. Model No. C240TM-B supplied by ThorLabs, Inc. (Newton, N.J.) can be used as the collimating lens. The collimating lens narrows the diverging beam from optical fiber 54 to an almost parallel beam approximately 3 mm in diameter Although this simple optical component cannot perfectly collimate the laser beam, it maintains the desired 3 mm diameter for a distance of about 5 cm from the output of the apparatus, which is sufficient for tissue soldering.

Figure 1A:
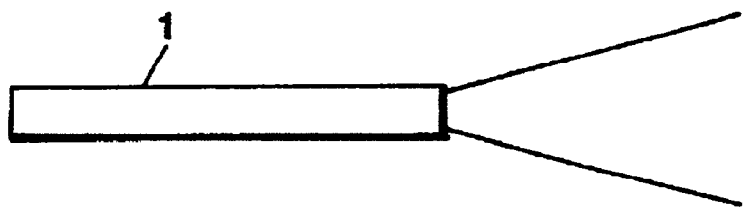
FIGS. 1a and 1b are schematic diagrams showing the divergence of an uncollimated and collimated laser beam, respectively.
Figure 1B:
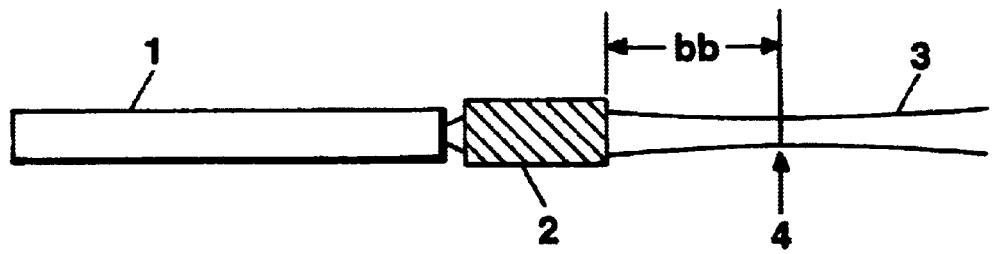
Figure 2A:
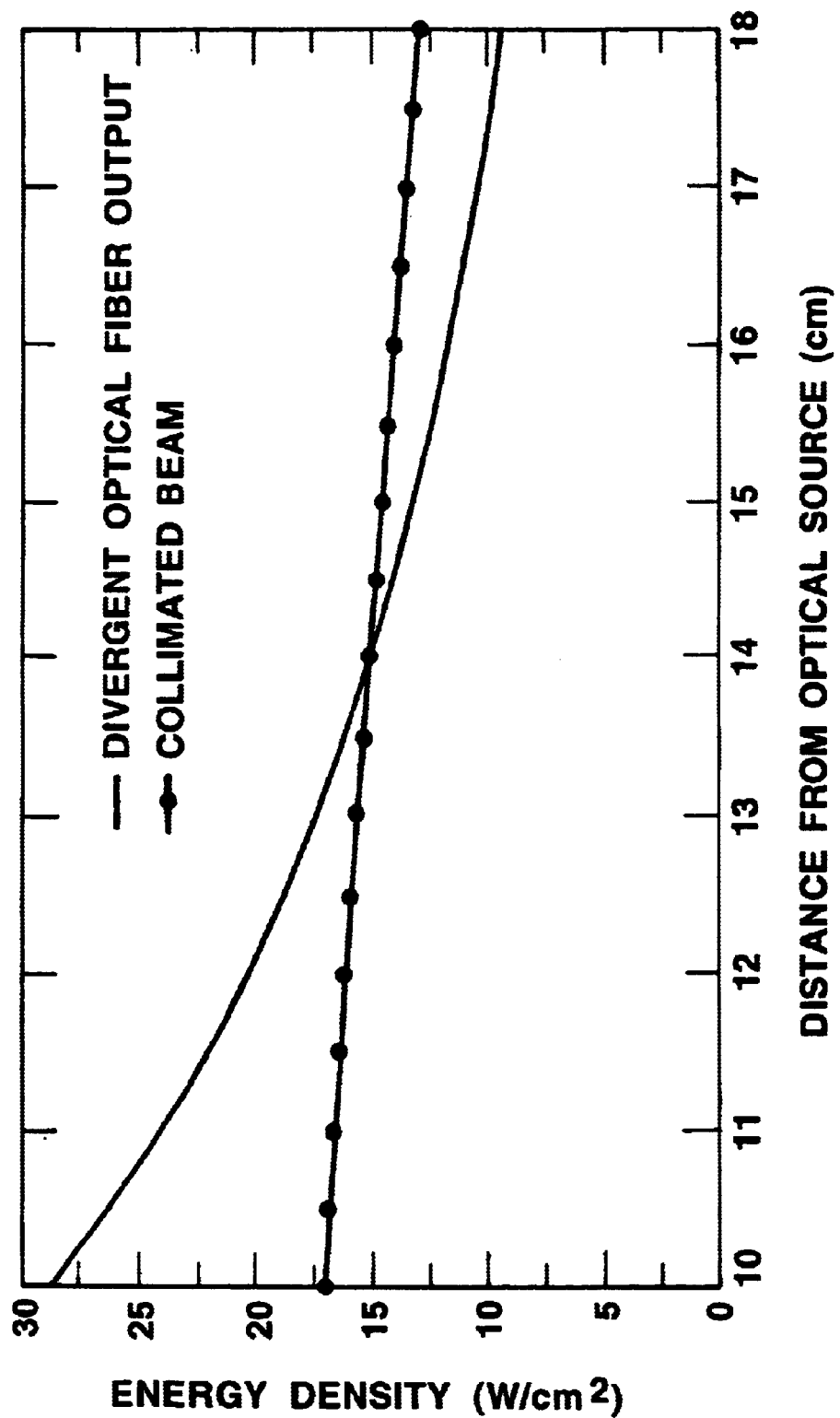
FIGS. 2a, 2b, 2c are plots of the power density as a function of distance from the source for uncollimated or collimated beams.

One of the more difficult aspects of the tissue soldering technique for a surgeon to master is the ability to keep a constant laser power density on the solder material using the standard optical fiber supplied with the large surgical laser sources. Since the output of the optical fiber is highly divergent, the power density delivered will depend strongly upon the distance from the wound to the optical fiber * output being held by the surgeon. As shown in FIG. 2a, if the desired output is 15 W/cm² (at a distance of about 14 cm) but the fiber comes closer to the wound by only 4 cm, then the power density from a non-collimated beam will nearly double. This may damage the skin and it could produce an inadequate seal by accidentally charring the solder.

Figure 7A:
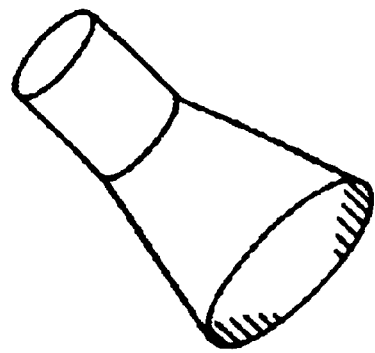
FIG. 7a shows a circular laser beam output.
Figure 7B:
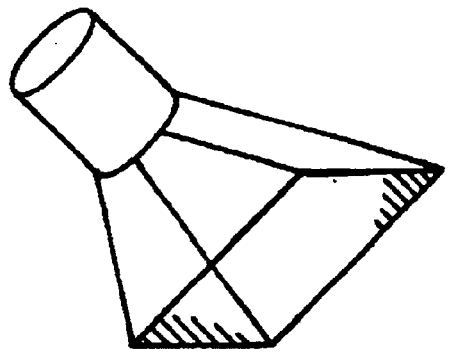
FIG. 7b shows a square/rectangular laser beam output.
Figure 7C:
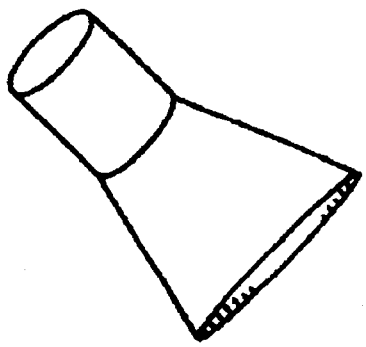
FIG. 7c shows a linear laser beam output.

The present invention could also use a structured laser beam to match up more closely with the solder area. FIGS. 7a–c show three different beam structures. The structure of the beam shown in FIG. 7a represents the circular collimated beam that was used in Example 2. FIG. 7b illustrates a square beam would cover the entire solder area with a constant power density, so that the surgeon would not have to move the laser around. Finally, the laser may produce an intense line that can be quickly scanned across the wound as shown in FIG. 7c.

EXAMPLE 2

The apparatus described in Example 1 can be used as follows to perform the LTS procedure. An albumin-based protein solder preparation can be used as described in U.S. Pat. Nos. 5,209,776 and 5,292,362, which are incorporated by reference herein. Briefly, a pasteurized 25% human albumin solution (The New York Blood Center, Melville Biologics Division, New York, N.Y.) is lyophilized. (dehydrated) under sterile conditions to powder form (2.5 g albumin) and reconstituted in 6.0 ml sterile water (42% albumin solution). After sterile filtration through a 0.2 m pore-sized filter, 200 $\mu$l aliquots of this solution are mixed with 100 $\mu$l of sterile ICG dye (CardioGreen, 2.5 mg/ml, Becton-Dickinson, Cockeyville, MD) and stored at –20° C. Twenty-four hours prior to use, 1 to 2 aliquots are thawed and combined with 200 $\mu$l of sodium hyaluronate (Healon, 10 mg/ml, Kabi Pharmacia Ophthalmics, Monrovia, Calf.) to make a total volume of 0.5 ml/aliquot. The final solution is vortexed for 30 seconds and stored in 1.5 ml conical tubes overnight.

When using a solder preparation containing ICG, the major wavelength output of the diode laser is 808±1 $\mu$m. Typical laser parameters for the tissue welding are approximately as follows: pulse duration=0.5 seconds, pulse "off" interval=0.1 to 0.5 seconds, power density=4 to 50 W/Cm², energy density 2 to 25 joules/cm².

Following completion of conventional suturing of the wound, laser activation of the albumin-based preparation over the suture line is performed. A thin printing layer of solder is applied over the sutured wound and laser activated until the solder is denatured. This can be seen as a green to tan color change. Applying thin layers of solder is essential, since thick application may allow for the top layer of the solder to heat and dry while the more important underlayer remains liquid. Such a solder will provide no additional strength to the closure. Solder is then reapplied in two or more layers, and laser activated as described.

Depending on the wound treated, tests can be performed to reveal the added strength of the solder-treated wound. For example, success of some urinary tract reconstruction can be determined using leak point pressure measurements, determined using an 18 gauge angiocatheter to measure intraluminal pressures while methylene blue dyed saline is infused at a rate of 20 to 30 ml/h.

EXAMPLE 3

Figure 2B:
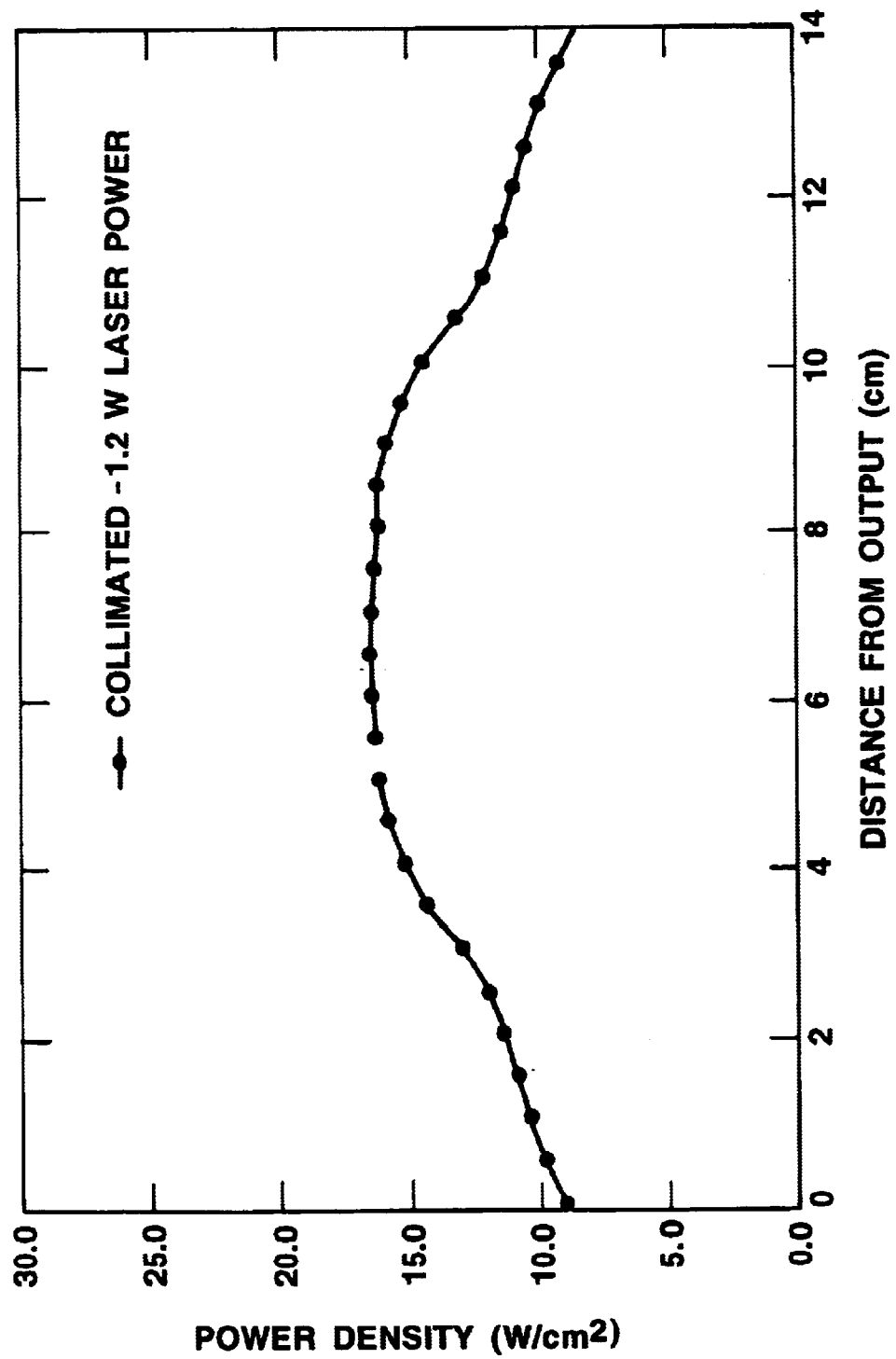
Figure 2C:
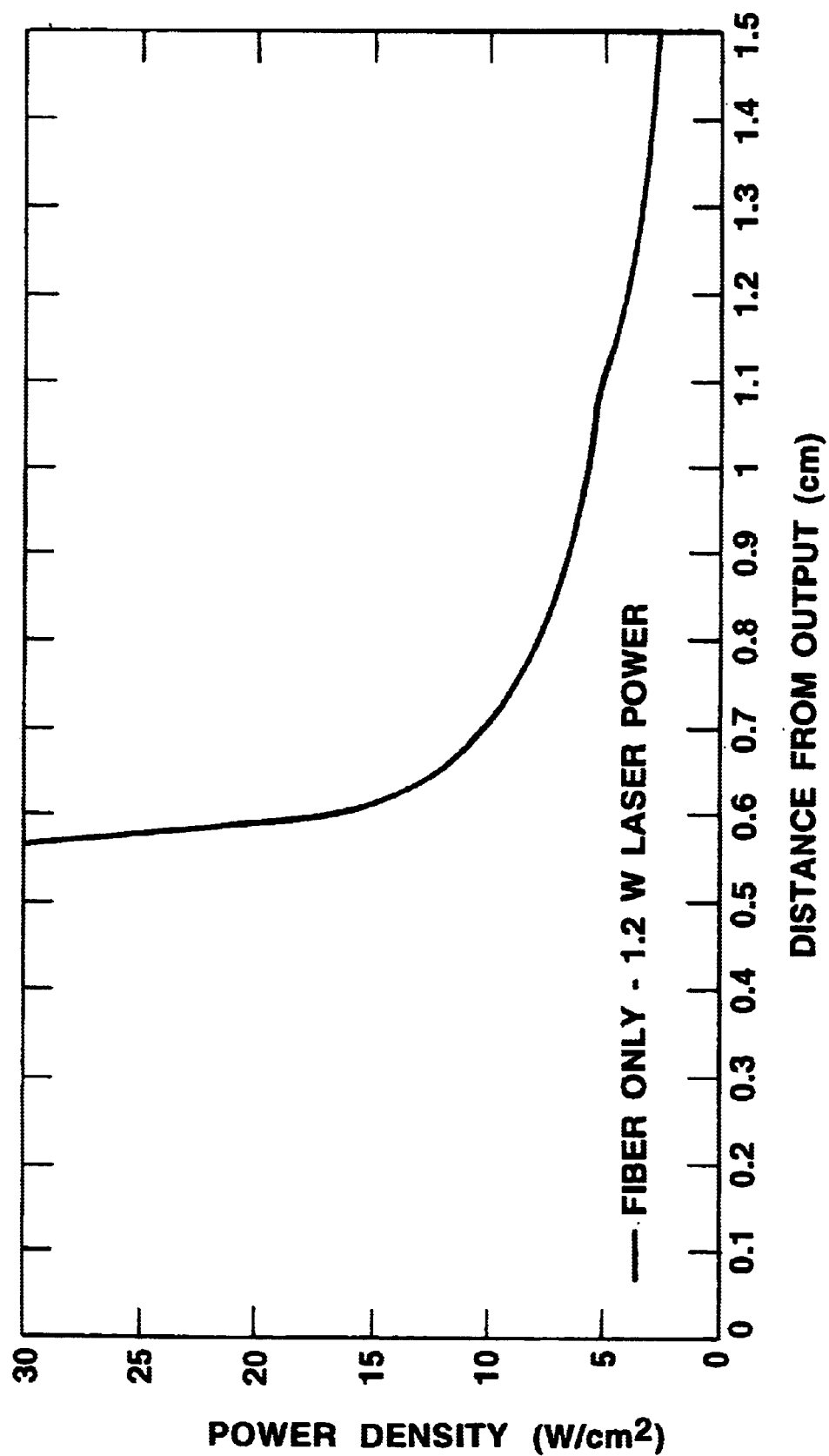
Figure 3:
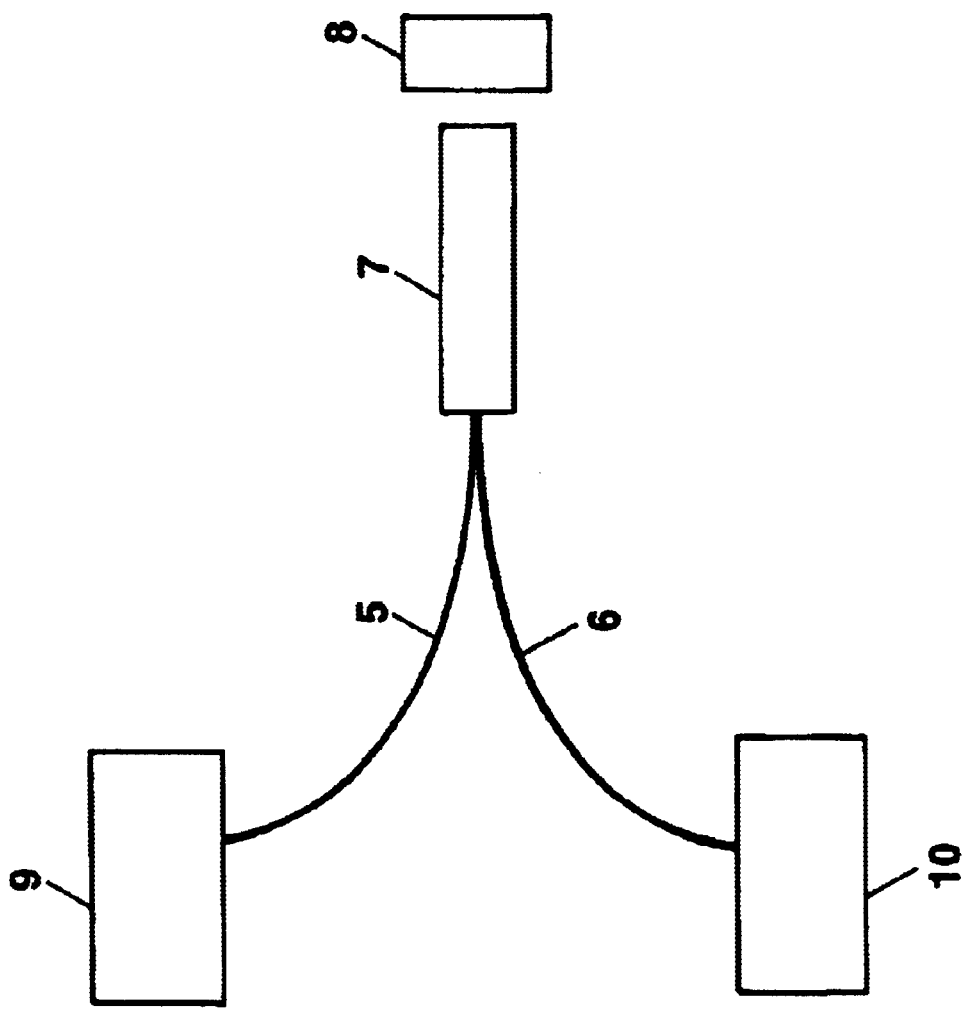
FIG. 3 is a schematic diagram of the present invention.
Figure 4A:
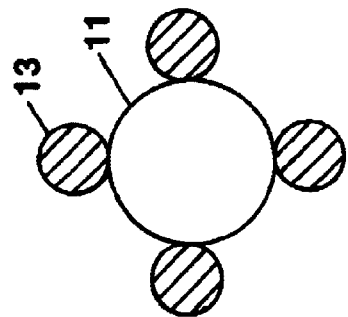
FIGS. 4a, 4b, 4c, 4d, 4e, 4f, 4g, 4h illustrate possible configurations of the visible and nonvisible beams of the present invention.
Figure 4B:
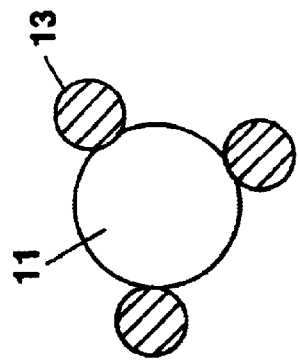
Figure 4C:
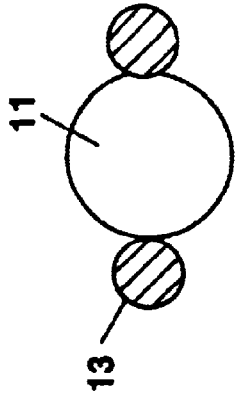
Figure 4D:
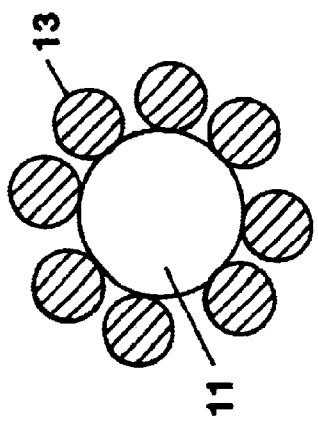
Figure 4E:
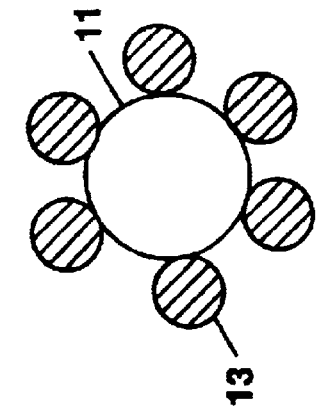
Figure 4H:
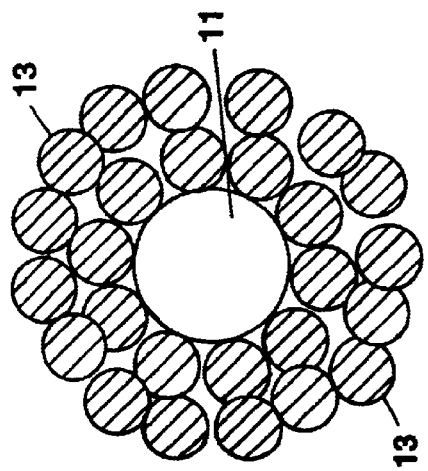
Figure 4G:
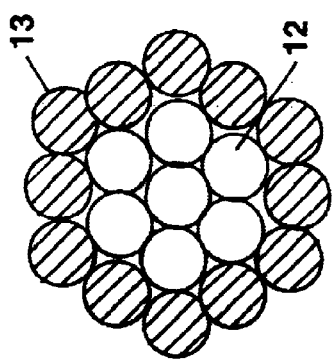
Figure 4F:
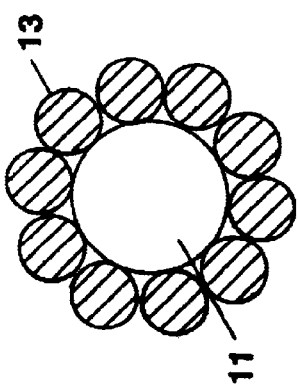
Figure 4I:
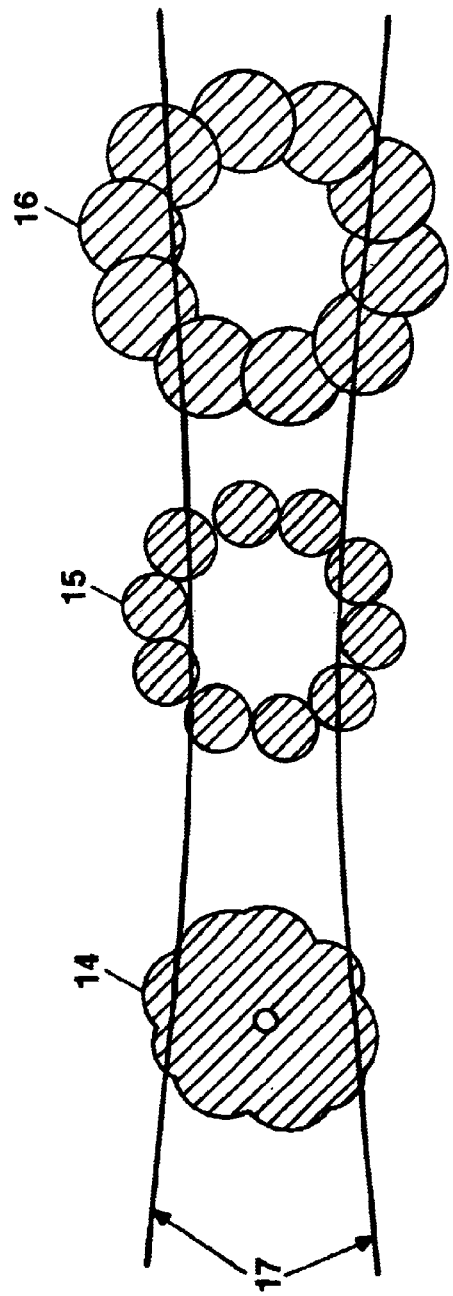
FIG. 4i illustrates how the visible light beam can be used to obtain both the precise location and the desired energy density for the nonvisible beam.
Figure 4K:
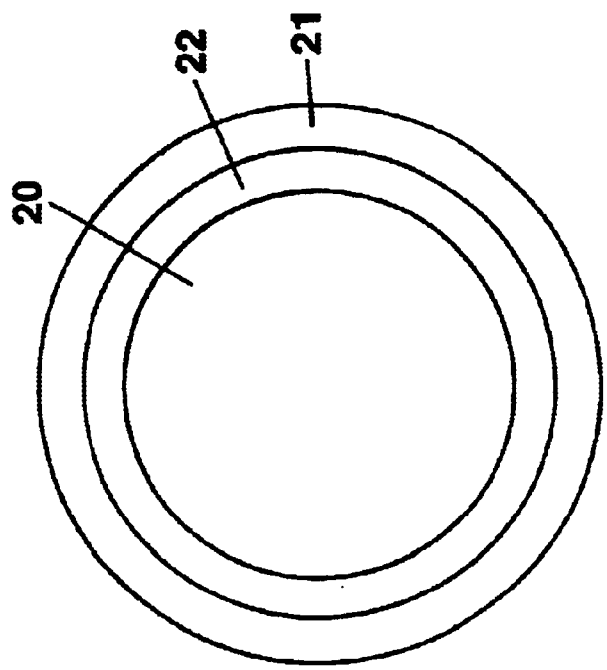
FIGS. 4j and 4k are a comparison of an optical fiber with a core and an outer cladding (FIG. 4j) and with a core, an inner cladding and an outer cladding (FIG. 4k).
Figure 4J:
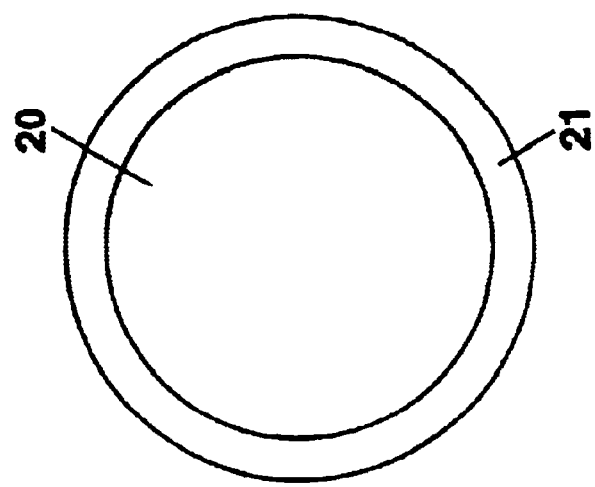
Figure 8:
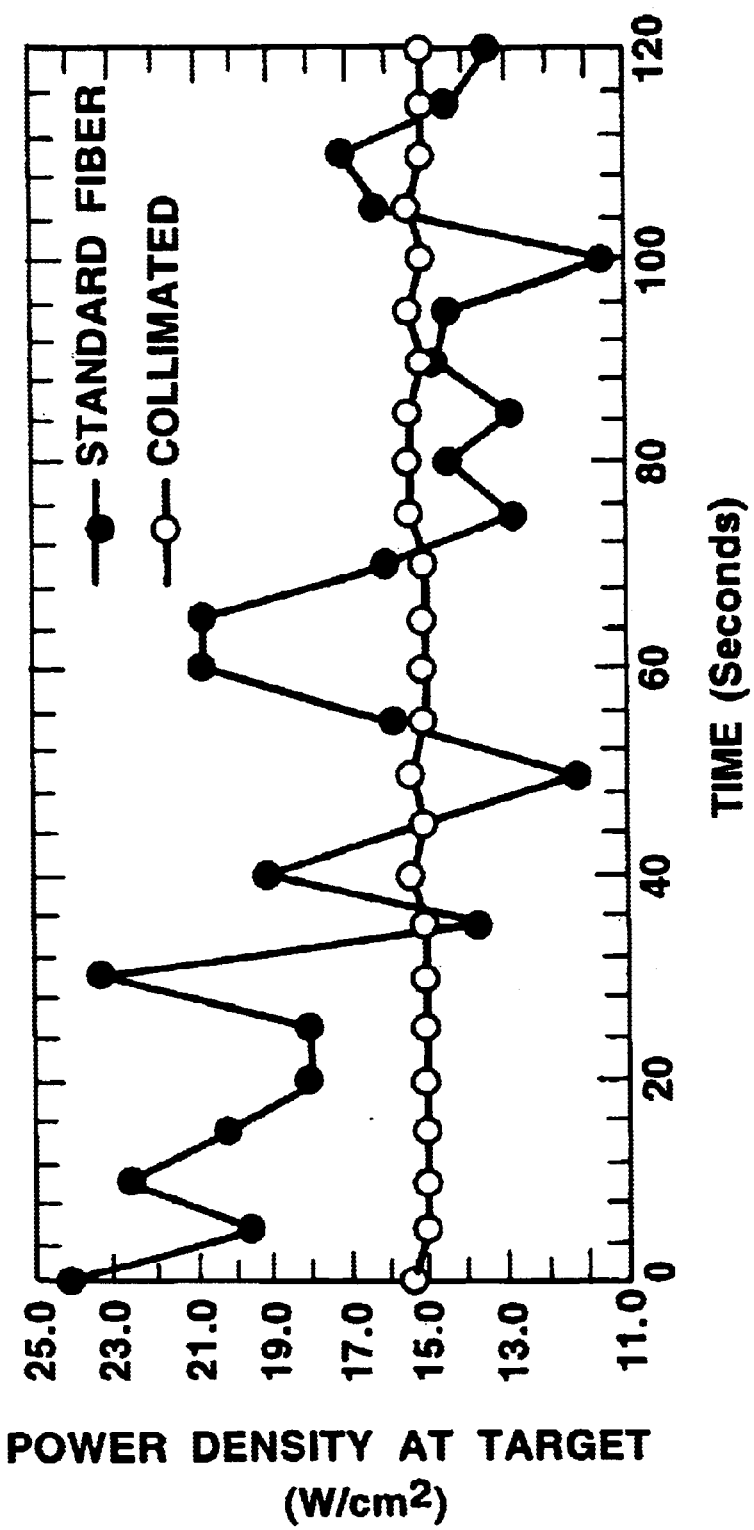
FIG. 8 is a plot of the power density at a target for the collimated beam of the present invention (open circles), compared to a plot of the power density for an uncollimated beam (dark circles).

To quantify how much of an improvement the collimated beam provides, a laboratory experiment was performed first with the original bare fiber delivery system, and then with the collimated fiber system. Each delivery fiber was moved slowly by hand over a simulated wound for a period of two minutes. The fluctuation in power density was monitored and the comparison is plotted as shown in FIG. 8. As evident from FIG. 8, the collimated fiber system has eliminated the dependence of power density on distance from the target (as also demonstrated by FIGS. 2a to 2c). These results demonstrate convincingly that the collimated beam is a much safer and more effective method for delivering beam power.

It is anticipated that alterations within the purview of one of ordinary skill in the art will be made to the above described preferred embodiment based on technology advances, for example, in the areas of laser diodes, rechargeable batteries, microelectronics, and such changes do not affect the scope of the disclosed invention.

What we claim is:

1. A laser system comprising:
   (a) a laser emitting nonvisible radiation optically connected to a first optical fiber, such that a nonvisible laser beam is transmitted through the optical fiber;
   (b) at least one visible light source optically connected to a plurality of second optical fibers, such that a visible light beam is transmitted through each of the plurality of second optical fibers, constituting a plurality of visible light beams;
   (c) collimating optics, constituting collimating means for collimating the nonvisible laser beam and the plurality of visible light beams, such than the plurality of visible light beams are in focus at a distance from the output of the collimating optics, said distance being the distance at which the nonvisible laser beam has an optimum power density; and
   (d) an optical fiber connector that connects the first optical fiber and the second optical fibers to the collimating optics, and that positions the first optical fiber at the center of the plurality of second optical fibers, such that the plurality of visible light beams surround and identify the position of the nonvisible laser beam.

2. The laser system of claim 1, wherein the variation in the power density of the nonvisible laser beam as a function of distance from the output of the collimating optics is less than 30% over a range of 3 cm on either side of an optimum distance.

3. The laser system of claim 1, wherein the collimated plurality of visible light beams are in focus at approximately an optimum distance.

4. The laser system of claim 1, wherein the collimating optics comprise a lens with focal lengths selected such that the nonvisible laser beam is in focus at an optimum distance.

5. The laser system of claim 4, wherein the collimating optics comprise a lens with characteristics such that the variation in the power density of the nonvisible laser beam is less than 50% over a range from one-half the optimum distance to one and a halt times the optimum distance.

6. The laser system of claim 1, wherein the plurality of second optional fibers is at least six second optical fibers.

7. The laser system of claim 1, wherein the plurality of second optical fibers consists of at least four optical fibers.

8. The laser system of claim 1 wherein after collimation the nonvisible laser beam is in an almost parallel beam 1.5 to 10 mm in diameter.

9. The laser system of claim 1, wherein the wavelength of the nonvisible laser beam is selected such that the nonvisible laser beam is absorbed by a chromophore.

10. The laser system of claim 1, wherein the wavelength of the nonvisible laser beam is selected such that the nonvisible laser beam is absorbed by a proteinbased solder.

11. A laser system comprising:
   (a) a laser emitting nonvisible radiation optically connected to a plurality of first optical fibers, such that a nonvisible laser beam is transmitted through each of the plurality of first optical fibers, constituting a plurality of nonvisible laser beams;
   (b) at least one visible light source optically connected to a plurality of second optical fibers, such that a visible light beam is transmitted through each of the plurality of second optical fibers constituting a plurality of visible light beams;
   (c) collimating optics, constituting collimating means for collimating the plurality of nonvisible laser beams and the plurality of visible light beams such that the plurality of visible light beams are in focus at a distance from the output of the collimating optics, said distance being the distance at which the plurality of nonvisible laser beams have an optimum power density; and
   (d) an optical fiber connector that connects the plurality of first optical fibers and the plurality of second optical fibers to the collimating optics and that positions the plurality of first optical fibers at the center of the plurality of second optical fibers, such that the plurality of visible light beams surround and identify the position of the plurality of nonvisible laser beams.

12. The laser system of claim 11, wherein the variation in the power density of the nonvisible laser beam as a function of distance from the output of the collimating optics is less than 30% over a range of 3 cm on either side of the optimum distance, and wherein the visible light beams are in focus at approximately the optimum distance.

13. The laser system of claim 11, wherein the plurality of second optical fibers consists of at least six optical fibers.

14. The laser system of claim 11, wherein after collimation each of the nonvisible laser beams is an almost parallel beam 1.5 mm to 10 mm in diameter.

15. A laser system comprising:
   (a) a laser diode that emits a nonvisible laser beam;
   (b) a first optical fiber receiving and transmitting the nonvisible laser beam; and
   (c) a plurality of second optical fibers;
   (d) at least one source of visible light optically coupled to the plurality of second optical fibers, each of the plurality of second optical fibers transmitting a visible light beam, constituting a plurality of visible light beams;
   (d) a fiber optic connector positioning the first optical fiber in the middle of the plurality of second optical fibers;
   (e) collimating optics, constituting collimating means, receiving the plurality of visible light beams and the nonvisible laser beam from the plurality of second optical fibers and the first optical fiber, the visible light beams and the nonvisible laser beam being directed at the collimating optics by the fiber optic connector;
   wherein the nonvisible laser beam is collimated by the collimating optics such that it has a relatively constant power density when the nonvisible laser beam is continuous, or a relatively constant energy density when the nonvisible laser beam is pulsed, over a range of 3 cm on either side of an optimum distance, and
   wherein the collimating optics constitute means for focusing the plurality of visible light beams at the optimum distance.

16. The laser system of claim 15, wherein the nonvisible laser beam has a diameter of 1.5 mm to 10 min at the optimum distance.

17. The laser system of claim 15, wherein the variation in the power density of the nonvisible laser beam is less than 50% over a range from one-half the optimum distance to one and a half times the optimum distance.

18. The laser system of claim 15, wherein the nonvisible laser beam has a linear structure.

19. The laser system of claim 15, wherein the nonvisible laser beam has a square structure.

20. A hand-held self-contained laser system compr
   (a) a laser diode in a fan-cooled heat sink for emitting a nonvisible laser beam;
   (b) a first optical fiber optically connected to the laser diode for transmitting the nonvisible laser beam;
   (c) a plurality of second optical fibers;
   (d) one or more light-emitting diodes emitting a visible light beam and optically connected to the plurality of second optical fibers for transmitting a plurality of visible light beams;
   (e) a fiber optic connector which positions the first optical fiber in the center of the plurality of second optical fibers;
   (f) collimating optics constituting collimating means, receiving the non visible-laser beam and the plurality of visible light beams, the non visible laser beam and the plurality of visible light beams being directed at the collimating optics by the fiber optic connector such that the nonvisible light beam is surrounded by the plurality of visible light beams that define the location of the nonvisible laser beam;
   (g) a rechargeable battery providing power to the laser diode and the one or more light-emitting diodes; and
   (h) an electronic circuit, electrically connected to a photodiode measuring the intensity of the nonvisible laser beam, said electronic circuit controlling the power to the laser diode by controlling the current to the laser diode according to a signal received from the photodiode representative of the intensity of the nonvisible laser beam,
   wherein the nonvisible laser beam has an optimum power density at an optimum distance from the collimating optics, said optimum distance being the distance at which the visible light beams are in focus.

21. The hand-held self-contained laser system of claim 20, further comprising a display panel comprising a means for indicating the status of the rechargeable battery.

22. The hand-held self-contained laser system of claim 20, wherein the nonvisible laser beam is an almost parallel beam approximately 1.5 mm to 10 mm in diameter.

23. The hand-held self-contained laser system of claim 20, wherein the power density of the nonvisible laser beam is 4 to 50 w/cm$^2$.

24. The hand-held self-contained laser system of claim 20, wherein the energy density of the nonvisible laser beam is 2 to 25 joules/cm$^2$.

25. The hand-held self-contained laser system of claim 20, wherein the light-emitting diodes emit green light.

26. The hand-held self-contained laser system of claim 20, wherein the wavelength of the nonvisible beam is 800±30 nanometers.

27. The hand-held self-contained laser system of claim 20, wherein the variation in the power density of the nonvisible laser beam is less than 50% over a range from one-half the optimum distance to one and a half times the optimum distance.

28. A laser system comprising:
(a) a plurality of lasers emitting nonvisible radiation, wherein each one of said plurality of lasers is optically connected to one of a plurality of first optical fibers, such that a nonvisible laser beam is transmitted through each of the plurality of first optical fibers, constituting a plurality of nonvisible laser beams;
(b) at least one visible light source optically connected to a plurality of second optical fibers, such that a visible light beam is transmitted through each of the plurality of second optical fibers, constituting a plurality of visible light beams;
(c) collimating optics, constituting collimating means for collimating the plurality of nonvisible laser beams and the plurality of visible light beams such that the plurality of visible light beams are in focus at a distance from the output of the collimating optics, said distance being the distance at which the plurality of nonvisible laser beams have an optimum power density; and
(d) an optical fiber connector that connects the plurality of first optical fibers and the second optical fibers to the collimating optics, and that positions the first optical fibers at the center of the plurality of second optical fibers, such that the plurality of visible light beams surround and identify the position of the plurality of nonvisible laser beams.

29. The laser system of claim 28, wherein the variation in the power density of the plurality of nonvisible laser beams as a function of distance from the output of the collimating optics is less than 30% over a range of 3 cam on either side of the optimum distance, and wherein the plurality of visible light beams are in focus at approximately the optimum distance.

30. A method for delivering energy to a target from a laser source emitting nonvisible radiation comprising the steps of:
optically connecting the laser source to a first optical fiber;
transmitting a nonvisible laser beam through the first optical fiber;
optically connecting at least one visible light source to a plurality of second optical fiber;
transmitting a visible light beam through each of the plurality of second optical fibers, constituting a plurality of visible light beams;
positioning the first optical fiber at the center of the plurality of second optical fibers;
directing the nonvisible laser beam and the plurality of visible light beams at collimating optics; collimating the nonvisible laser beam and the plurality of visible light beams, such that the visible light beams are in focus at a distance from the output of the collimating optics at which the nonvisible laser beam has a power density substantially equal to an optimum power density, and, such that the plurality of visible light beams surround and identity the position of the non-visible laser beam;
whereby the dependence of power density at the target on the distance from the output of the collimating optics is significantly reduced.

31. A method for delivering energy to a target from a laser source_emitting nonvisible radiation comprising the steps of:
optically connecting the laser source to a plurality of first optical fibers;
transmitting a nonvisible laser beam through each of the plurality of first optical fibers;
optically connecting at least one visible light source to a plurality of second optical fibers;
transmitting a visible light beam through each of the plurality of second optical fibers constituting a plurality of visible light beams;
positioning the plurality of first optical fibers at the center of the plurality of second optical fibers;
directing the nonvisible laser beam and the plurality of visible light beams at collimating optics;
collimating the nonvisible laser beam and the plurality of visible light beams, such that the plurality of visible light beams are in focus at a distance from the output of the collimating optics at which the nonvisible laser beam has a power density substantially equal to an optimum power density, and, such that the plurality of visible light beams surround and identify the position of the nonvisible laser beam;
whereby the dependence of power density at the target on the distance from the output of the collimating optics is significantly reduced.

32. A method for delivering energy to a target from a plurality of laser sources emitting nonvisible radiation comprising the steps of:
optically connecting the plurality of laser sources to a plurality of first optical fibers;
transmitting a non visible laser beam through each of the plurality of first optical fibers, constituting a plurality of non visible laser beams;
optically connecting at least one visible light source to a plurality of second optical fiber;
transmitting a visible light beam through each of the plurality of second optical fibers, constituting a plurality of visible light beams;
positioning the plurality of first optical fibers at the center of the plurality of second optical fibers;
directing the nonvisible laser beam and the plurality of visible light beams at collimating optics;
collimating the nonvisible laser beam and the plurality of visible light beams, such that the plurality of visible light beams are in focus at a distance from the output of the collimating optics at which the nonvisible laser beam has a power density substantially equal to an optimum power density, and, such that the plurality of visible light beam surround and identify the position of the nonvisible laser beam;
whereby the dependence of power density at the target on the distance from the output of the collimating optics is significantly reduced.

33. A method for delivering energy to a target from a handheld self-contained laser source comprising the steps of:
optically connecting a laser diode to a first optical fiber, the laser diode emitting a nonvisible laser beam;
providing the laser diode with a fan-cooled heat sink;
transmitting a non visible laser beam through the first optical fiber;
optically connecting at least one visible light emitting diode to a plurality of second optical fiber;
providing power to the laser diode and the at least one visible light emitting diode from a rechargeable battery;

transmitting a visible light beam through each of the plurality of second optical fibers, constituting a plurality of visible light beams;

positioning the first optical fiber at the center of the plurality of second optical fibers;

directing the nonvisible laser beam and the plurality of visible light beams at collimating optics;

collimating the nonvisible laser beam and the plurality of visible light beams, such that the plurality of visible light beams are in focus at a distance from the output of the collimating optics at which the nonvisible laser beam has a power density substantially equal to an optimum power density, and, such that the visible light beams surround and identify the position of the nonvisible laser beam;

electrically connecting an electronic circuit to a photodiode;

measuring intensity of the nonvisible laser beam with the photodiode;

controlling the power to the laser diode with the electronic circuit according to the signal received from the photodiode;

wherein the power to the laser diode is controlled by controlling current to the laser diode; and, whereby the dependence of power density at the target on the distance from the output of the collimating optics is significantly reduced.

34. The method of claim 33 further comprising the step of:
indicating the status of the rechargeable battery.

35. A laser system comprising:
(a) at least one laser emitting nonvisible radiation optically connected to a first radiation transmitting optical sub-system, said first radiation transmitting optical sub-system transmitting and outputting at least one nonvisible laser beam;
(b) at least one visible light source optically connected to a second radiation transmitting optical sub-system, said second radiation transmitting optical sub-system transmitting and outputting at least one visible light beam;
(c) collimating means that collimate the output of said first radiation transmitting optical sub-system and the output of said second radiation transmitting optical sub-system such that the output of said second radiation transmitting optical sub-system is in focus at a distance where the output of said first radiation transmitting optical sub-system has an optimum power density;
(d) positioning means that position said first radiation transmitting optical sub-system and said second radiation transmitting optical sub-system such that said second radiation transmitting optical sub-system surrounds said first radiation transmitting optical sub-system.

36. The laser system of claim 35 wherein said at least one laser emitting nonvisible radiation comprises one laser emitting nonvisible radiation;
wherein said first radiation transmitting optical sub-system comprises a central core of an optical fiber, said optical fiber having the central core, an inner cladding capable of transmitting a visible light beam and an outer cladding, a laser beam of nonvisible radiation being transmitted through and outputted from the central core of the optical fiber;
wherein said at least one visible light source comprises one visible light source;
wherein said second radiation transmitting optical sub-system comprises the inner cladding of the optical fiber, such that a visible light beam being transmitted through and outputted from the inner cladding;
wherein said collimating means comprise collimating optics collimating the laser beam of nonvisible radiation and the visible light beam, such that the visible light beam is in focus at a distance from the output of the collimating optics, said distance being the distance at which the laser beam of nonvisible radiation has an optimum power density, and, such that the visible light beam surrounds and identifies the position of the laser beam of nonvisible radiation;
and wherein the fiber constitutes the positioning means.

37. The laser system of claim 35, wherein the variation in the power density of the nonvisible laser beam as a function of distance from an output of the collimating means is less than 30% over a range of 3 cm on either side of an optimum distance.

38. The laser system of claim 35, wherein the visible light beam is in focus at approximately an optimum distance.

39. The laser system of claim 35, wherein the collimating means have a focal length selected such that the nonvisible laser beam is in focus at an optimum distance.

40. The laser system of claim 39, wherein the variation in the power density of the nonvisible laser bean is less than 50% over a range from one-half the optimum distance to one and a half times the optimum distance.

41. The laser system of claim 35, wherein after collimation the nonvisible laser beam is an almost parallel beam 1.5 mm to 10 mm in diameter.

42. The laser system of claim 35, wherein the wavelength of the nonvisible laser beam is selected such that the nonvisible laser beam is absorbed by a chromophore.

43. The laser system of claim 35, wherein the wavelength of the nonvisible laser beam is selected such that the nonvisible laser beam is absorbed by a protein based solder.

* * * * *

UNITED STATES PATENT AND TRADEMARK OFFICE
CERTIFICATE OF CORRECTION

PATENT NO. : 6,724,958 B1
DATED : April 20, 2004
INVENTOR(S) : John D. German et al.

It is certified that error appears in the above-identified patent and that said Letters Patent is hereby corrected as shown below:

<u>Title page, Item [54] and Column 1, line 1</u>,
Title, should read -- HANDHELD LASER SYSTEM EMITTING VISIBLE AND NON-VISIBLE RADIATION --

<u>Column 9</u>,
Line 16, portion of line reading "optical fibers constituting" should read -- optical fibers, constituting --
Line 27, portion of line reading "collimating optics and" should read -- collimating optics, and --

Signed and Sealed this

Sixth Day of July, 2004

JON W. DUDAS
*Acting Director of the United States Patent and Trademark Office*